United States Patent [19]
Saunders

[11] Patent Number: 5,176,696
[45] Date of Patent: Jan. 5, 1993

[54] HANDLES FOR MICROSURGICAL INSTRUMENTS

[76] Inventor: Myles L. Saunders, 415 Evelyn Pl., Beverly Hills, Calif. 90210

[21] Appl. No.: 767,474

[22] Filed: Sep. 30, 1991

[51] Int. Cl.⁵ .................................................. A61B 17/32
[52] U.S. Cl. .................................... 606/174; 606/167; 606/210; 30/340
[58] Field of Search ............... 606/167, 170, 174, 175, 606/181, 185, 186, 190, 191, 205, 206, 207, 210; 30/340, 341

[56] References Cited

U.S. PATENT DOCUMENTS

| | | | |
|---|---|---|---|
| 288,096 | 11/1883 | Morgan . | |
| 987,095 | 3/1911 | Bonta . | |
| 2,370,026 | 2/1945 | Elia | 30/341 |
| 2,540,255 | 2/1951 | Graves . | |
| 2,669,991 | 2/1954 | Curutchet | 606/205 |
| 2,669,993 | 2/1954 | Curutchet | 606/205 |
| 3,407,816 | 10/1968 | Curutchet | 606/174 X |
| 3,557,792 | 1/1971 | Rubin | 606/206 X |
| 4,127,112 | 11/1978 | Sherlock et al. | 606/205 X |
| 4,165,795 | 8/1979 | Heifetz | 606/174 |
| 4,433,687 | 2/1984 | Burke et al. . | |
| 4,462,404 | 7/1984 | Schwarz et al. | 606/206 |
| 4,644,651 | 2/1987 | Jacobsen . | |
| 4,674,501 | 6/1987 | Greenberg . | |
| 4,949,717 | 8/1990 | Shaw | 606/174 X |
| 5,002,554 | 3/1991 | Korber . | |

FOREIGN PATENT DOCUMENTS

| | | | |
|---|---|---|---|
| 291238 | 4/1916 | Fed. Rep. of Germany . | |
| 1105210 | 11/1955 | France | 606/207 |

Primary Examiner—Robert A. Hafer
Assistant Examiner—Sam Rimell
Attorney, Agent, or Firm—Thomas I. Rozsa

[57] ABSTRACT

The present invention is improved handles incorporated with a microsurgical instrument. The microsurgical instrument has a pair of crisscrossed members each having a forward functional portion and a rearward portion. Each of the rearward portions of the pair of crisscrossed members is substantially widened for accommodating the fingers of a surgeon's hand, such that the fingers are positioned parallel to the general longitudinal profile of the microsurgical instrument. The forward functional portions may be microsurgical scissors, microsurgical needle holders, microsurgical Aneurysmen clips, and the like.

32 Claims, 2 Drawing Sheets

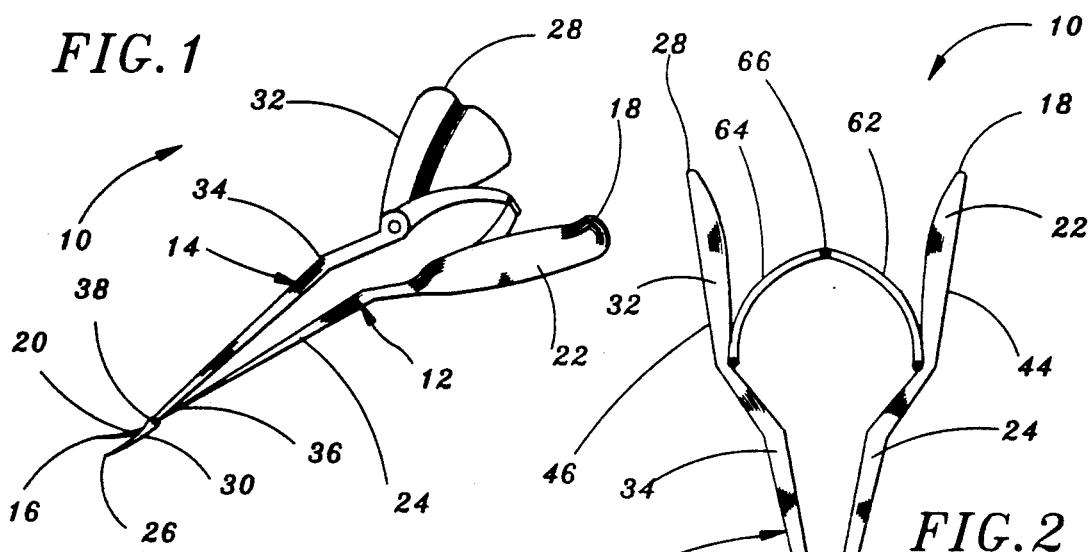
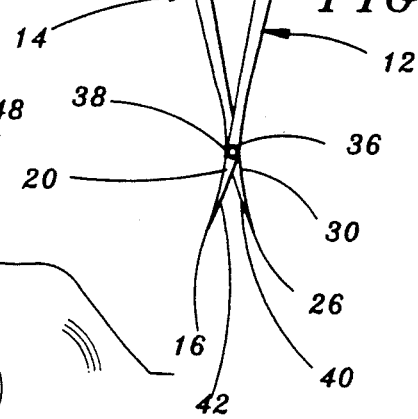
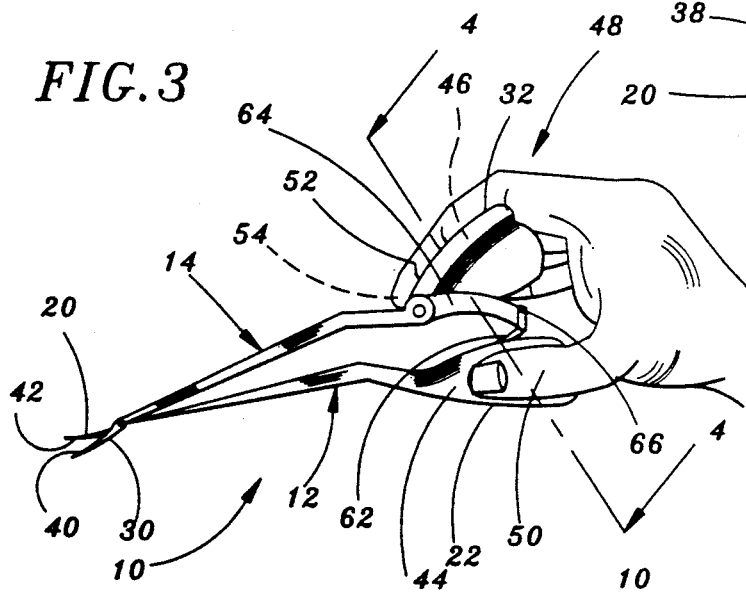
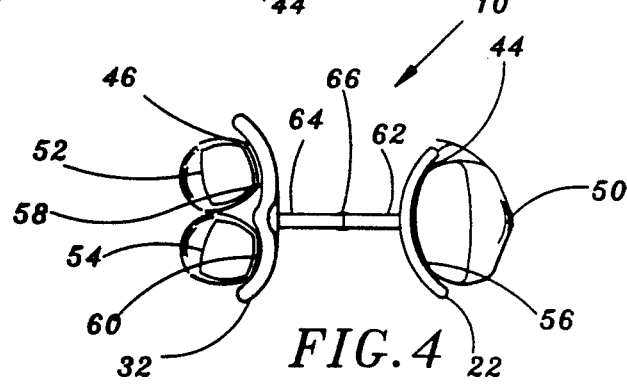
FIG.1
FIG.2
FIG.3
FIG.4

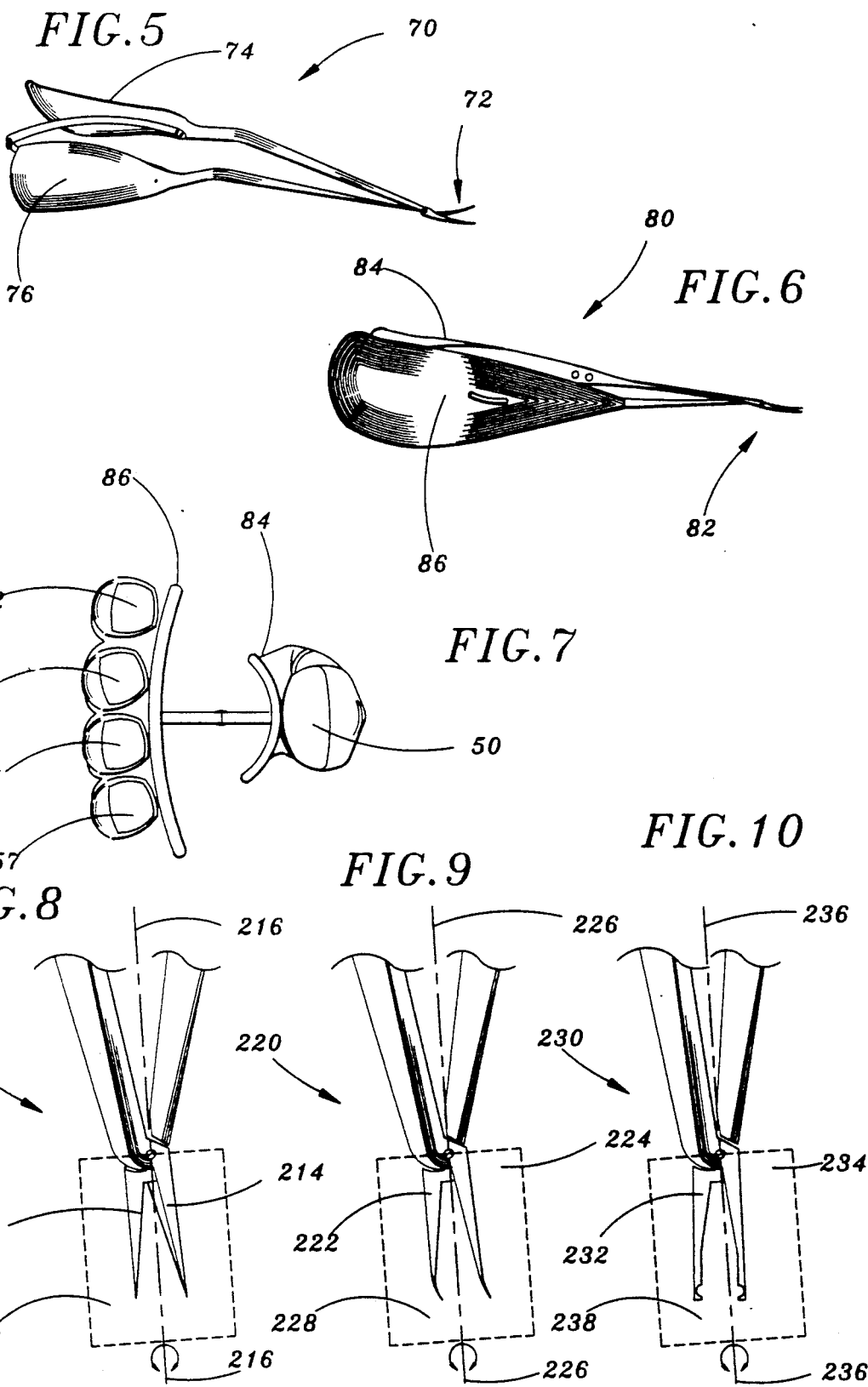

HANDLES FOR MICROSURGICAL INSTRUMENTS

BACKGROUND OF THE INVENTION

1. Field of the Invention

The present invention generally relates to the field of microsurgical instruments. More particularly the present invention relates to the field of improved handles for microsurgical instruments.

2. Description of the Prior Art

The following prior art patents generally relate to the field of microsurgical and other clipping devices.

1. U.S. Pat. No. 5,002,554 issued to Korber on Mar. 26, 1991 for "Microscissors Device And Anastomotic Repair Technique" (hereafter the "Korber Patent").

2. U.S. Pat. No. 4,674,501 issued to Greenberg on Jun. 23, 1987 for "Surgical Instrument" (hereafter the "Greenberg Patent").

3. U.S. Pat. No. 4,644,651 issued to Jacobsen on Feb. 24, 1987 for "Instrument For Gripping Or Cutting" (hereafter the "Jacobsen Patent").

4. U.S. Pat. No. 4,433,687 issued to Burke et al. on Feb. 28, 1984 for "Microsurgical Scissors" (hereafter the "Burke Patent").

5. U.S. Pat. No. 4,165,745 issued to Heifetz on Aug. 28, 1979 for "Surgical Manipulator" (hereafter the "Heifetz Patent").

6. U.S. Pat. No. 3,407,816 issued to Curutchet on Oct. 26, 1968 for "Surgical Instrument Handle" (hereafter the "Curutchet Patent").

7. U.S. Pat. No. 2,540,255 issued to Graves on Feb. 5, 1951 for "Fruit Clipper" (hereafter the "Graves Patent").

8. U.S. Pat. No. 987,095 issued to Bonta on Mar. 14, 1911 for "Fruit Clipper" (hereafter the "Bonta Patent").

9. U.S. Pat. No. 288,096 issued to Morgan on Nov. 6, 1883 for "Fruit Picker" (hereafter the "Morgan Patent").

10. German Patent No. 291,238 issued on Apr. 7, 1916 (hereafter the "German Patent").

The Heifetz Patent discloses a surgical manipulator having a pair of elongated prongs 32 and 33, each having a first end and a second end. The two elongated prongs 32 and 33 are resiliently biased away from each other by a biasing means 45 which "may be separate from or integral with the device" (Column 3, Lines 38 and 39). One particular feature of the Heifetz Patent is that the first ends of the two elongated prongs 32 and 33 are joined together to form a spindle 60. Therefore the Heifetz Patent is generally a pair of tweezers, although in one embodiment the second ends of the two elongated prongs 32 and 33 can hingeably support a pair of scissors 80 (FIG. 6).

The Burke Patent discloses a microsurgical scissors specially designed for arthroscopic knee surgery. The first cutting blade, shaft blade 13, is disposed at the forward end of an elongated hollow shaft 11. The second cutting blade, the rod cutting blade 14, is disposed at the forward end of a rod 12 which in turn is disposed within the hollow shaft 11. By pressing a sleeve 10B, the surgeon can rotate the rod 12 through the gear engagement, which in turn actuates the rod blade 14 to move in an arcuate path past the shaft blade 13 for providing a shearing action of the scissors. The Burke Patent performs the cutting in a rotary cutting action.

The Jacobsen Patent discloses a surgical instrument having a fixed jaw 12 integrally formed at one end of an elongated base 11 and a movable jaw 13 pivoted on the elongated base 11 adjacent to the fixed jaw 12. The movable jaw 13 is controlled by a handle 28, which is pivoted on the opposite end of the elongated base 11, through an elongated actuating shank 22. The Jacobsen Patent utilizes three separate elongated members: the base 11, the handle 28 and the actuate shank 22.

The Greenberg Patent discloses a surgical instrument having a pair of scissors 72 and 76 respectively provided on the ends of two axially mating and relatively slidable elongated shafts 54 and 56, which are in turn activated by a pair of handles 12 and 16. The fixed shaft 54 and the movable shaft 56 "are conjointly rotatable about their common central axis" by rotating an indexing wheel 38, such that the cutting plane of the pair of scissors 72 and 76 can be rotatively changed.

The Korber Patent discloses a microsurgical scissors having two elongated arms 3 and 5 pivoted at a joint 7. Two cutting edges are provided respectively on the two elongated arms 3 and 5, between their first ends and the joint 7. At the second ends of the two elongated arms 3 and 5 there are two spring arms 3A and 5A provided for biasing the second ends of the two elongated arms 3 and 5 away from each other. The two spring arms 3A and 5A are hingeably attached to each other at joint 9. Furthermore, knurled surfaces 11 and 13 are provided on the two elongated arms 3 and 5 adjacent to their second ends for easy gripping of the device.

The Morgan Patent discloses a fruit picker having outwardly disposed grooves provided on its handles for adapting the user's fingers.

The Bonta Patent discloses a fruit clipper having finger loops 4 provided on its handles for adapting the user's fingers.

The Graves Patent discloses a fruit clipper also having finger loops 16 provided on its handles for adapting the user's fingers.

The Curutchet Patent discloses an early surgical instrument handle having extra members 13 and 14 with grooves for adapting the surgeon's fingers.

The German Patent discloses a scissor-type apparatus apparently having biasing springs e and f attached to the two handles and hinged to each other.

Many of the above-reference prior art patents, including the Curutchet Patent, the Greenberg Patent, the Burke Patent and the Jacobsen Patent, have complicated structures and numerous components. Others, including the Morgan Patent, the Bonta Patent and the Graves Patent, are not designed and constructed for microsurgical purposes, but rather for fruit clipping.

The Korber Patent is a microsurgical scissors device. It has two elongated arms 3 and 5 pivoted at a joint 7. Adjacent the first ends of the two elongated arms 3 and 5 there are two cutting edges provided for functioning as scissors. At the second ends of the two elongated arms 3 and 5 there are two spring arms 3A and 5A provided for biasing the two elongated arms 3 and 5. The problem with the Korber Patent microsurgical scissors is that when a surgeon holds the handle portions of the two elongated arms 3 and 5, his fingers are generally perpendicular to the two elongated arms 3 and 5. In other words, when handling the microsurgical scissors device in this fashion, the elongated arms of the microsurgical scissors device is generally not aligned with the general lengthwise direction of the surgeon's fingers. handling the microsurgical scissors device in this fashion sometimes limits the flexibility and sensitivity that the surgeon has for controlling the cutting orientation and strength because of the natural bone structure and movement of a human hand. In addition, the elongated biasing springs 3A and 5A, which extend from the rear ends of the two elongated arms 3 and 5 respectively, sometimes interfere with the surgeon's palm or wrist as he tries to orient the instrument in certain positions during microsurgical operations.

The Jacobsen Patent provides a surgical gripping or cutting instrument, wherein when held by a surgeon, the elongated arms of the gripping or cutting instrument are generally aligned with the lengthwise direction of the surgeon's thumb and index finger. This arrangement gives the surgeon more precise control over the instrument, because it more readily adapts to the natural bone structure and movement of a human hand. However, the Jacobsen Patent instrument is relatively complicated and heavy because it has extra bar members. In addition, the tiny biasing coil springs, such as coil springs 38 and 48, and the tiny apertures holding the coil springs, sometimes make it difficult to clean the instrument thoroughly.

Therefore, although various types of microsurgical devices have been disclosed in the prior art, it is still desirable to have improved simple structure handles for microsurgical instruments.

SUMMARY OF THE INVENTION

The present invention is improved handles for microsurgical instruments.

The functional portion of many microsurgical instruments has two hinged members. For example, as shown in FIGS. 8, 9 and 10 respectively, the function portion 210 of a microsurgical scissors instrument has two cutting members 212 and 214, the function portion 220 of a microsurgical holders instrument has two forceps members 222 and 224, and the function portion 230 of a microsurgical clip instrument has two clamping members 232 and 234.

When these paired members are closed, they coincide with the respective longitudinal axis of the microsurgical device. For example, when the two cutting members 212 and 214 are closed, they coincide with the longitudinal axis 216 of the microsurgical scissors device; when the two forceps members 222 and 224 are closed, they coincide with the longitudinal axis 226 of the microsurgical holder device, and when the two clamping members 232 and 234 are closed, they coincide with the longitudinal axis 236 of the microsurgical clip device. However, when these paired members are opened, each pair defines a respective plane. For example, when the two cutting members 212 and 214 are opened, they define a plane 218; when the two forceps members 222 and 224 are opened, they define a plane 228, and when the two clamping members 232 and 234 are opened, they define a plane 238.

The above-described planes illustrate the orientation of the microsurgical instruments. In many situations, a surgeon needs to orient the microsurgical instrument in a certain way by rotating the plane about the longitudinal axis. For example, in order to cut a thread which happens to be parallel to plane 218, a surgeon has to rotate the microsurgical scissors device about its longitudinal angle 216, such that the plane 218 defined by the two cutting members 212 and 214 is rotating about the longitudinal angle 216 for about 90 degrees so it is perpendicular to the thread.

It has been discovered, according to the present invention, that if a surgeon holds the traditional handles of a microsurgical instrument in his hand, then the surgeon's fingers are generally perpendicular to the longitudinal axis of the microsurgical device, which makes it very hard for the surgeon to rotate the two open members of the microsurgical device about the longitudinal axis without departing from its original direction.

It is therefore an object of the present invention to provide improved handles for various microsurgical instruments, which improved handles are constructed in a unique way, such that when a surgeon holds the improved handles of a microsurgical instrument in the surgeon's hand, the surgeon's fingers are generally parallel to the longitudinal axis of the microsurgical instrument, which makes it very easy for the surgeon to rotate the two open members of the microsurgical instrument about the longitudinal axis without departing from its original direction.

It is a further object of the present invention to provide improved handles for various microsurgical instruments, which improved handles are constructed as simple and light as possible, to enable a surgeon to control the microsurgical instrument more easily in very delicate or precise surgical operations. It is desirable to retain the basic structure of a hinged design, wherein two elongated members are hingeably attached in a crisscross manner, since such a simple structure does not require many complicated and heavy components.

It is also an object of the present invention to provide improved handles for various microsurgical instruments which improved handles enable a surgeon to control the microsurgical scissors instrument more precisely in very delicate or precise surgical operations. Each improved handle of the microsurgical scissors instrument will have a substantially widened outer surface. A longitudinal groove may be provided on the substantially widened outer surface of one handle for accommodating the thumb of a surgeon's one hand, and two longitudinal grooves may be provided on the substantially widened outer surface of the other handle for accommodating the index and middle fingers of the surgeon's same hand. As the surgeon holds the improved handles, one handle is engaged with and positioned parallel to the thumb of the surgeon's one hand, and the other handle is engaged with and positioned parallel to the index and middle fingers of the surgeon's same hand. Holding the microsurgical instrument in this manner provides the surgeon much more precise and sensitive control over the movement and orientation of the scissors instrument in very delicate or precise microsurgical operations.

It is an additional object of the present invention to provide an improved handle with an improved biasing mechanism. The function of the biasing mechanism is to keep the two improved handles of a microsurgical instrument in a balanced position, wherein the two functional members of the microsurgical instrument are spaced apart when the improved handles are not compressed.

Since the improved handles of the microsurgical instrument are disposed between the thumb and the index and middle fingers and engaged longitudinally thereon, the rear ends of the two improved handles of the microsurgical instrument are disposed in proximity to the palm of the surgeon's hand. To prevent any interference between the parts of the microsurgical instrument and the surgeon's palm or wrist, the improved biasing mechanism of the present invention microsurgical instrument is disposed between the two improved handles, without extending beyond the rear ends of the two improved handles. Therefore, the surgeon has much greater flexibility in oriently the present invention microsurgical scissors instrument.

It is a further object of the present inventoin to incorporate the improved handles with an improved biasing mechanism into as many microsurgical instruments as possible, including microsurgical scissors, microsurgical holders, microsurgical forceps, microsurgical clipping instruments and microsurgical gripping instruments, and other like microsurgical instruments.

It is another object of the present invention to incorporate the improved handles with improved biasing mechanism into other similar crisscross devices, such as scissors, forceps, clippers, etc.

Further novel features and other objects of the present invention will become apparent from the following detailed description, discussion and the appended claims, taken in conjunction with the drawings.

BRIEF DESCRIPTION OF THE DRAWINGS

Referring particularly to the drawings for the purpose of illustrating only and not limitation, there is illustrated:

FIG. 1 is a perspective view of a microsurgical scissors instrument which incorporates one of the preferred embodiments of the present invention improved handles with an improved biasing spring.

FIG. 2 is a top plan view of the microsurgical scissors instrument which incorporates one of the preferred embodiments of the present invention improved handles with an improved biasing spring.

FIG. 3 is a perspective view showing that one of the preferred embodiments of the present invention improved handles of the microsurgical scissors instrument are held by a surgeon's hand.

FIG. 4 is a cross-sectional view taken along line 4—4 of FIG. 3.

FIG. 5 is a perspective view of a microsurgical holders instrument which incorporates an alternative embodiment of the present invention improved handles.

FIG. 6 is a perspective view of a microsurgical clippers instrument which incorporates another alternative embodiment of the present invention improved handles.

FIG. 7 is a cross sectional view showing how the other alternative embodiment of the present invention improved handles of the microsurgical scissors instrument is held by a surgeon's hand.

FIG. 8 is an enlarged partial view of the forward function portion of the microsurgical scissors instrument shown in FIGS. 1 through 3.

FIG. 9 is an enlarged partial view of the forward function portion of the microsurgical holders instrument shown in FIG. 5.

FIG. 10 is an enlarged partial view of the forward function portion of the microsurgical clippers instrument shown in FIG. 6.

DESCRIPTION OF THE PREFERRED EMBODIMENT

Although specific embodiments of the present invention will now be described with reference to the drawings, it should be understood that such embodiments are by way of example only and merely illustrative of but a small number of the many possible specific embodiments which can represent applications of the principles of the present invention. Various changes and modifications obvious to one skilled in the art to which the present invention pertains are deemed to be within the spirit, scope and contemplation of the present invention as further defined in the appended claims.

Referring to FIGS. 1 and 2, there is shown at 10 a microsurgical scissors instrument which incorporates the present invention improved handles. The microsurgical scissors instrument 10 has two elongated members 12 and 14. The first elongated member 12 has a front end 16 and a rear end 18. Between its front end 16 and rear end 18, the first elongated member 12 may be divided into three portions: a cutting portion 20 adjacent to the front end 16, a handle portion 22 adjacent to the rear end 18, and an arm portion 24 interconnecting the cutting portion 20 and the handle portion 22. Similarly, the second elongated member 14 also has a front end 26 and a rear end 28. Between its front end 26 and rear end 28, the second elongated member 14 may also be divided into three portions: a cutting portion 30 adjacent to the front end 26, a handle portion 32 adjacent to the rear end 28, and an arm portion 34 interconnecting the cutting portion 30 and the handle portion 32. The arm portions 24 and 34 of the two elongated members are substantially longer than the cutting portions 20 and 30 and the handle portions 22 and 32 of the two elongated members. The arm portions 24 and 34 of the two elongated members may have any suitable configuration. Preferably, they are bent and have a generally L-shaped configuration. The two elongated members 12 and 14 may be made of any suitable material such as stainless steel.

The two elongated members 12 and 14 are hingeably attached together in a crisscross manner at a joint 36 between their respective cutting portions 20 and 30 and their arm portions 24 and 34. The hingeable attachment may be made by any suitable means. In a simple form, the two elongated members 12 and 14 are hinged together by a small mounting pin 38. The small mounting pin 38 may be a separate pin, or integrally formed with either the first elongated member 12 or the second elongated member 14. When the two elongated members 12 and 14 are hingeably attached in this manner, the opening and closing of the two cutting portions 20 and 30 of the two elongated members 12 and 14 can be controlled by operating the two handle portions 22 and 32 of the two elongated members 12 and 14, i.e., separating or compressing the two handle portions 22 and 32 of the two elongated members 12 and 14, respectively.

The respective lengths and shapes of the cutting portions 20 and 30 of the two elongated members 12 and 14 are substantially similar and both are very thin and narrow, as required for microsurgical operations. In one of the preferred embodiments, the tapered tips of the cutting portions 20 and 30 are slightly bent up for more precise operation. The cutting portion 20 of the first elongated member 12 has a sharp inner edge 42, and the cutting portion 30 of the second elongated member 14 also has a sharp inner edge 40. When the two handle portions 22 and 32 of the two elongated members 12 and 14 are compressed toward each other, the cutting portions 20 and 30 of the two elongated members 12 and 14 will close toward each other, and consequently their sharp inner edges 42 and 40 will cross each other to perform a scissors action.

The novel feature of the present invention is that the handle portions 22 and 32 of the two elongated members 12 and 14, respectively, each have a substantially widened outer surface, denoted as 44 and 46 respectively, for accommodating the fingers of a surgeon's hand 48. As shown in FIGS. 3 and 4, the thumb 50 of the surgeon's one hand 48 is engaged onto the widened outer surface 44 of the handle portion 22 of the first elongated member 12, and the index and middle fingers 52 and 54 of the surgeon's same hand 48 are engaged onto the widened outer surface 46 of the handle portion 32 of the second elongated member 14. Moreover, there is a longitudinal groove 56 provided on the widened outer surface 44 of the handle portion 22 of the first elongated member 12 for better adapting the thumb 50 of the surgeon's hand 48, and there are two longitudinal grooves 58 and 60 provided on the widened outer surface 46 of the handle portion 32 of the second elongated member 14 for better adapting the index and middle fingers 52 and 54 of the surgeon's hand 48. The thumb groove 56 extends longitudinally along the entire length or almost the entire length of the handle portion 22 of the first elongated member 12, and the index finger and middle finger grooves 58 and 60 extend longitudinally along the entire length or almost the entire length of the handle portion 32 of the second elongated member 14. Therefore, when the surgeon's fingers 50, 52 and 54 are engaged with the finger grooves 56, 58 and 60 respectively, the handle portions 22 and 32 of the two elongated members 12 and 14 are generally parallel with the surgeon's fingers 50, 52 and 54, especially parallel with the surgeon's thumb 50 and index finger 52. Consequently the two elongated members 12 and 14 are generally aligned with the longitudinal direction of the surgeon's thumb 50 and index finger 52. This arrangement enables the surgeon's hand 48 to orient and operate the microsurgical scissors instrument 10 in a much more suitable manner, which is more fitting with the natural bone structure and movement of the human hand. In addition, the finger grooves 56, 58 and 60 act to prevent the slipping between the surgeon's fingers 50, 52 and 54 and the widened outer surfaces 44 and 46 of the handle portions 22 and 32 of the two elongated member 12 and 14, and to provide the required sensitive feel and precise control over the microsurgical scissors instrument 10.

The exact configurations of the substantially widened outer surface 44 and 46 of the handle portions 22 and 32 of the two elongated members 12 and 14 may vary. In one of the preferred embodiments of the present invention, the widths of the handle portions 22 and 32 are gradually increased, being widest at the rear ends 18 and 28. Since the handle portion 22 of the first elongated member 12 is engaged with only the thumb 50 of the surgeon's hand, and the handle portion 32 of the second elongated member 14 is engaged with both the index finger 52 and the middle finger 54, the overall width of the handle portion 32 of the second elongated member 14 is greater than the overall width of the handle portion 22 of the first elongated member 12. It is understood that the embodiment shown in FIG. 3 is designed for a right-handed surgeon. For a left-handed surgeon, the configurations of the handle portions 22 and 32 are simply reversed.

A biasing mechanism is provided for the present invention improved handles incorporated with the microscissors instrument 10 to keep the two elongated members 12 and 14 in a balanced position as they are hingeably attached. In a preferred balanced position, the handle portions 22 and 32 of the two elongated members 12 and 14 are spaced apart, so that the sharp inner edges 42 and 40 of the cutting portions 20 and 30 of the two elongated members 12 and 14 are open and ready for cutting. When the sugeon's fingers apply forces onto the outer surfaces 44 and 46 of the handle portions 22 and 32 of the two elongated members 12 and 14 to compress them toward each other against the force of the biasing mechanism, the cutting portions 20 and 30 of the two elongated members 12 and 14 will move close to each other, and their sharp inner edges 42 and 40 will preform a scissors action. When the surgeon's fingers are relaxed, the force of the biasing mechanism will separate the handle portions 22 and 32 of the two elongated member 12 and 14, and the sharp inner edges 42 and 40 of the cutting portions 20 and 30 of the two elongated members 12 and 14 will be open again and ready for the next cutting.

In the preferred embodiment of the improved handles of the present invention incorporated with the microscissors instrument 10, the biasing mechanism includes two thin and narrow spring plates 62 and 64. The two thin and narrow spring plates 62 and 64 are respectively attached to the handle portions 22 and 32 of the two elongated members 12 and 14 at a respective one of their ends and hingeably attached at a joint 66 at their other ends, as shown in the figures. The two thin and narrow spring plates 62 and 64 may by removably or permanently attached to the two elongated members 12 and 14. The exact location of attachment may vary. The biasing mechanism may be of other forms, such as a coil spring.

Using two hinged spring plates is conventional in the art, particularly in microsurgical instruments, since they are simple, light and easy to clean. A typical prior art arrangement of the biasing spring plates is disclosed in the Kober Patent, where the two thin spring plates 3A and 5A extend from the rear ends of the two elongated members 11 and 13, and are hingeably attached at a joint 9. However, this arrangement is not suitable for the microscissors instrument 10, because the latter is held in a completely different manner. When the microscissors instrument 10 is held in the manner shown in FIG. 3, anything beyond the rear ends 18 and 28 of the two elongated members 12 and 14 will interfere with the palm of the surgeon's hand 48. Therefore an important feature of the biasing mechanism of the microsurgical scissors instrument 10 is that the biasing mechanism is disposed between the handle portions 22 and 32 without extending beyond the rear ends 18 and 28 of the two elongated members 12 and 14. In the preferred embodiment of the microsurgical scissors instrument 10, one end of the first spring plate 62 is attached to the first elongated member 12 at a location between the handle portion 22 and the arm portion 24, and one end of the second spring plate 64 is attached to the second elongated member 14 at a location between the handle portion 32 and the arm portion 34. It is further provided that the length of each spring plate is shorter than the overall length of each handle portion of the two elongated members 12 and 14. Therefore, even when the handle portions 22 and 32 are fully compressed, the hinged joint 66 of the two spring plates 62 and 64 will still not extend beyond the rear ends 18 and 28 of the two elongated members 12 and 14.

An enlarged partial view of the forward function portion of a microsurgical scissors instrument is shown in FIG. 8 at 210, which has two cutting members 212 and 214. However, it will be appreciated that to incorporate the improved handles of the present invention into a microsurgical scissors instrument is only one of many possible uses of the improved handles. Another two commonly used microsurgical instruments are shown in FIGS. 5 and 6 as examples of the wide application of the present invention improved handles.

Shown in FIG. 5 at 70, an alternative embodiment of the present invention improved handles is incorporated with a microsurgical holders instrument. The forward functional portion 72 of the microsurgical holders instrument comprises two curved holding members. The two widened handle portions 74 and 76 are similar to the ones for the microsurgical scissors instrument 10 shown in FIGS. 1 through 3, but without the optional longitudinal grooves. The handle portions are curved in a concave shape and are curved toward each other. Shown in FIG. 6 at 80, there is another alternative embodiment of the present invention improved handles, which is incorporated with a microsurgical clippers instrument. The forward functional portion 82 of the microsurgical holders instrument comprises two curved holding members. The two handle portions 84 and 86 are again widened. However, as shown in FIG. 7, while one of the two handle portions, handle portion 86, is adapted to accommodate the thumb 50 of a surgeon's one hand, the other one of the two handle portions, handle portion 86, is dramatically widened to accommodate all four other fingers of the surgeon's hand. The width and shape of the handle portion 86 is constructed to be comfortably engaged by the surgeon's index finger 52, middle finger 54, ring finger 55 and little finger 57, as these four fingers are naturally positioned. The handle portions are curved in a convex shape and are curved away from each other.

The essential feature of these embodiments of the present invention improved handles shown in FIGS. 5 through 7 is the same as the one shown in FIGS. 1 through 4, that is, to allow the surgeon's fingers to lie generally longitudinally along the same general longitudinal axis of the body of the microsurgical instrument held by the fingers. When one's fingers are so oriented, it is very easy to rotate the microsurgical instrument as held by the surgeon's fingers about the longitudinal axis of the microsurgical instrument. This essential feature enables the surgeon to gain precise control over the orientation of the forward functional portion of the microsurgical instruments.

FIGS. 9 and 10 are enlarged partial views of the foward function portions of the microsurgical instruments shown in FIGS. 5 and 6, respectively. The forward functional portion 220 of the microsurgical needle holders instrument is shown in FIG. 9, and the forward functional portion 230 of the microsurgical Aneurysmen clips instrument is shown in FIG. 10. Of course these are only examples of the various microsurgical instruments and other suitable instruments that can be incorporated with the present invention improved handles.

The present invention has many advantageous features including: (a) it has a simple construction without many complex components; (b) it is easy to cleaned and maintain; (c) it enables the surgeon to control operations more precisely; and (d) it will not interfere with other parts of the surgeon's hand.

Defined in detail, the present invention is a microsurgical instrument, comprising: (a) a first elongated member having a front end, a rear end, a functioning portion adjacent to its front end, a handle portion adjacent to its rear end, and an arm portion interconnecting its functioning portion and its handle portion; (b) a second elongated member having a front end, a rear end, a functioning portion adjacent to its front end, a handle portion adjacent to its rear end, and an arm portion interconnecting its functioning portion and its handle portion; (c) connecting means for hingeably attaching said first and second elongated members in a crisscross manner at a joint between their said functioning portions and said arm portions; (d) said handle portions of said first and second elongated members each having a substantially widened outer surface; (e) said substantially widened outer surface of said handle portion of said first elongated member having a longitudinal groove for accommodating the thumb of a surgeon's one hand, and said substantially widened outer surface of said handle portion of said second elongated member having two longitudinal grooves for accommodating the index and middle fingers of the surgeon's same hand; and (f) biasing means attached and disposed between said handle portions of said first and second elongated members without extending beyond said rear ends of said first and second elongated members for keeping said first and second elongated members in a balanced position.

In one of the preferred embodiments of the present invention: (a) said arm portions of said first and second elongated members are bent and have a generally L-shaped configuration; (b) said connecting means include a small mounting pin; (c) said small mounting pin is integrally formed with one of said first and said second elongated members; (d) said longitudinal groove on said substantially widened outer surface of said handle portion of said first elongated member for accommodating the thumb of a surgeon's one hand extends the entire length of said handle portion of said first elongated member; (e) said longitudinal groove on said substantially widened outer surface of said handle portion of said first elongated member for accommodating the thumb of a surgeon's one hand extends a substantial length of said handle portion of said first elongated member; (f) said two longitudinal grooves on said substantially widened outer surface of said handle portion of said second elongated member for accommodating the index and middle fingers of the surgeon's same hand extend the entire length of said handle portion of said second elongated member; (g) said two longitudinal grooves on said substantially widened outer surface of said handle portion of said second elongated member for accommodating the index and middle fingers of the surgeon's same hand extend a substantial length of said handle portion of said second elongated member; (h) said biasing means include two thin and narrow spring plates each having a first end and a second end, where the first ends of the first and second thin and narrow spring plates are respectively attached to said two elongated members at respective locations between their said handle portions and said arm portions, and the second ends of the two thin and narrow spring plates are hingeably attached to each other at a location not beyond said rear ends of said first and second elongated members; (i) said first ends of said two thin and narrow spring plates are permanently attached to said first and second elongated members at respective locations between their said handle portions and said arm portions; and (j) the respective length of said two thin and narrow spring plates are shorter than the respective length of said handle portions of said first and second elongated members.

The forward portion of the present invention device is the functional portion of the instrument. In one of the preferred embodiments, the functional portion is a microscissors instrument. It will be appreciated that the functional portion of the present invention may be other types of devices such as a microsurgical needle holder instrument or a microsurgical Aneurysmen clips instrument, where the inner edges of the forward portions of the two elongated members are not sharp but have other suitable configurations as shown in FIGS. 9 and 10, respectively.

Defined broadly, the present invention is a microsurgical instrument, comprising: (a) a pair of crisscrossed members each having a forward portion and a rearward portion; (b) said forward portions being functional portions of said microsurgical instrument; (c) one of said rearward portions of said pair of crisscrossed members being widened for accommodating the thumb of a surgeon's one hand such that the thumb is positioned generally parallel with a generally longitudinal axis of said microsurgical instrument, and the other one of said rearward portions of said pair of crisscrossed members being substantially widened to accommodate other fingers of the surgeon's same hand, such that these fingers are also positioned generally parallel with the generally longitudinal axis of said microsurgical instrument; and (d) biasing means attached to said pair of crisscrossed members and disposed between said rearward portions of said pair of crisscrossed members for keeping said pair of crisscrossed members in a balanced position.

Defined even more broadly, the present invention is a microsurgical instrument, comprising: (a) a pair of hingeably attached members each having a forward portion and rearward portion; (b) said forward portions of said pair of hingeably attached members having means for performing at least one microsurgical function; and (c) said rearward portions of said pair of hingeably attached members each being substantially widened for engaging with at least one of the five fingers of a surgeon's one hand, such that the at least one finger being engaged is positioned generally parallel to a generally longitudinal profile of said microsurgical instruments.

Of course the present invention is not intended to be restricted to any paricular form or arrangement, or any specific embodiment disclosed herein, or any specific use, since the same may be modified in various particulars or relations without departing from the spirit or scope of the claimed invention hereinabove shown and described of which the apparatus shown is intended only for illustration and for disclosure of an operative embodiment and not to show all of the various forms or modifications in which the present invention might be embodied or operated.

The present invention has been described in considerable detail in order to comply with the patent laws by providing full public disclosure of at least one of its forms. However, such detailed description is not intended in any way to limit the broad features or principles of the present invention, or the scope of patent monopoly to be granted.

What is claimed is :

1. A microsurgical instrument, comprising:
   a. a first elongated member having a front end, a rear end, a functioning portion adjacent to its front end, a handle portion adjacent to its rear end, and an arm portion interconnecting its functioning portion and its handle portion;
   b. a second elongated member having a front end, a rear end, a functioning portion adjacent to its front end, a handle portion adjacent to its rear end, and an arm portion interconnecting its functioning portion and its handle portion;
   c. connecting means for hingeably attaching said first and second elongated members in a crisscross manner at a joint between their said functioning portions and said arm portions;
   d. said handle portions of said first and second elongated members each having a substantially widened outer surface;
   e. said substantially widened outer surface of said handle portion of said first elongated member having a longitudinal groove for accommodating the thumb of a surgeon's one hand, and said substantially widened outer surface of said handle portion of said second elongated member having two longitudinal grooves for accommodating the index and middle fingers of the surgeon's same hand;
   f. said longitudinal groove on said substantially widened outer surface of said handle portion of said first elongated member for accommodating the thumb of a surgeon's one hand extends the entire length of said handle portion of said first elongated member; and
   g. biasing means attached and disposed between said handle portions of said first and second elongated members without extending beyond said rear ends of said first and second elongated members for keeping said first and second elongated members in a balanced position.

2. The microsurgical instrument as defined in claim 1, wherein said arm portions of said first and second elongated members are bent and have a generally L-shaped configuration.

3. The microsurgical instrument as defined in claim 1, wherein said connecting means includes a small mounting pin.

4. The microsurgical instrument as defined in claim 3, wherein said small mounting pin is integrally formed with one of said first and said second elongated members.

5. The microsurgical instrument as defined in claim 1, wherein said two longitudinal grooves on said substantially widened outer surface of said handle portion of said second elongated member for accommodating the index and middle fingers of the surgeon's same hand extend the entire length of said handle portion of said second elongated member.

6. The microsurgical instrument as defined in claim 1, wherein said biasing means includes two thin and narrow spring plates each having a first end and a second end, where the first ends of the first and second thin and narrow spring plates are respectively attached to said two elongated members at respective locations between their said handle portions and said arm portions, and the second ends of the two thin and narrow spring plates are hingeably attached to each other at a location not beyond said rear ends of said first and second elongated members.

7. The microsurgical instrument as defined in claim 6 wherein said first ends of said two thin and narrow spring plates are permanently attached to said first and second elongated members at respective locations between their said handle portions and said arm portions.

8. The microsurgical instrument as defined in claim 6 wherein the respective length of said two thin and narrow spring plates are shorter than the respective length of said handle portions of said first and second elongated members.

9. The microsurgical instrument as defined in claim 1 wherein said functional portions of said first and second elongated members are microsurgical scissors.

10. The microsurgical instrument as defined in claim 6 wherein said functional portions of said first and second elongated members are microsurgical needle holders.

11. The microsurgical instrument as defined in claim 1 wherein said functional portions of said first and second elongated members are microsurgical Aneurysmen clips.

12. A microsurgical instrument, comprising:
   a. a pair of crisscrossed members each having a forward portion and a rearward portion;
   b. said forward portions being functional portions of said microsurgical instrument;
   c. said rearward portions of said pair of crisscrossed members being substantially widened and having two-dimensional curvature for accommodating a surgeon's one hand; and
   d. biasing means attached to said pair of crisscrossed members and disposed between said rearward portions of said pair of crisscrossed members for keeping said pair of crisscrossed members in a balanced position.

13. The microsurgical instrument as defined in claim 12 wherein said two-dimensional curvatures of said substantially widened rearward portions of said pair of crisscrossed members are concave curvatures, such that said rearward portions are curved toward each other.

14. The microsurgical instrument as defined in claim 12 wherein said two-dimensional curvatures of said substantially widened rearward portions of said pair of crisscrossed members are convex curvatures, such that said rearward portions are curved away from each other.

15. The microsurgical instrument as defined in claim 12 wherein said biasing means includes a pair of thin and narrow spring plates respectively attached to said pair of crisscrossed members and hingeably attached to each other.

16. The microsurgical instrument as defined in claim 15 wherein the respective length of said pair of thin and narrow spring plates are shorter than the respective length of said rearward portions of said pair of crisscrossed members.

17. The microsurgical instrument as defined in claim 12 wherein said forward functional portions of said pair of crisscrossed members are microsurgical scissors.

18. The microsurgical instrument as defined in claim 12 wherein said forward functional portions of said pair of crisscrossed members are microsurgical needle holders.

19. The microsurgical instrument as defined in claim 12 wherein said forward functional portions of said pair of crisscrossed members are microsurgical Aneurysmen clips.

20. The microsurgical instrument as defined in claim 12 wherein said rearward portions of said crisscrossed members are each generally curved in a convex shape and are curved away from each other.

21. The microsurgical instrument as defined in claim 12 wherein said rearward portions of said crisscrossed members are each generally curved in a concave shape and are curved toward each other.

22. A microsurgical instrument, comprising:
   a. a first elongated member having a front end, a rear end, a functioning portion adjacent to its front end, a handle portion adjacent to its rear end, and an arm portion interconnecting its functioning portion and its handle portion;
   b. a second elongated member having a front end, a rear end, a functioning portion adjacent to its front end, a handle portion adjacent to its rear end, and an arm portion interconnecting its functioning portion and its handle portion;
   c. connecting means for hingeably attaching said first and second elongated members in a crisscross manner at a joint between their said functioning portions and said arm portions;
   d. said handle portions of said first and second elongated members each having a substantially widened outer surface;
   e. said substantially widened outer surface of said handle portion of said first elongated member having a longitudinal groove for accommodating the thumb of a surgeon's one hand, and said substantially widened outer surface of said handle portion of said second elongated member having two longitudinal grooves for accommodating the index and middle fingers of the surgeon's same hand;
   f. said two longitudinal grooves on said substantially widened outer surface of said handle portion of said second elongated member for accommodating the index and middle fingers of the surgeon's same hand extend the entire length of said handle portion of said second elongated member; and
   g. biasing means attached and disposed between said handle portions of said first and second elongated members without extending beyond said rear ends of said first and second elongated members for keeping said first and second elongated members in a balanced position.

23. The microsurgical instrument as defined in claim 22 wherein said arm portions of said first and second elongated members are bent and have a generally L-shaped configuration.

24. The microsurgical instrument as defined in claim 22 wherein said connecting means includes a small mounting pin.

25. The microsurgical instrument as defined in claim 22 wherein said small mounting pin is integrally formed with one of said first and said second elongated members.

26. The microsurgical instrument as defined in claim 22 wherein said longitudinal groove on said substantially widened outer surface of said handle portion of said first elongated member for accommodating the thumb of a surgeon's one hand extends the entire length of said handle portion of said first elongated member.

27. The microsurgical instrument as defined in claim 22 wherein said biasing means includes two thin and narrow spring plates each having a first end and a second end, where the first ends of the first and second thin and narrow spring plates are respectively attached to said two elongated members at respective locations between their said handle portions and said arm portions, and the second ends of the two thin and narrow spring plates are hingeably attached to each other at a location not beyond said rear ends of said first and second elongated members.

28. The microsurgical instrument as defined in claim 27 wherein said first ends of said two thin and narrow spring plates are permanently attached to said first and second elongated members at respective locations between their said handle portions and said arm portions.

29. The microsurgical instrument as defined in claim 27 wherein the respective length of said two thin and narrow spring plates are shorter than the respective length of said handle portions of said first and second elongated members.

30. The microsurgical instrument as defined in claim 22 wherein said functional portions of said first and second elongated members are microsurgical scissors.

31. The microsurgical instrument as defined in claim 22 wherein said functional portions of said first and second elongated members are microsurgical needle holders.

32. The microsurgical instrument as defined in claim 22 wherein said functional portions of said first and second elongated members are microsurgical aneurysm clips.

* * * * *